(12) United States Patent
Greenberg et al.

(10) Patent No.: US 6,533,798 B2
(45) Date of Patent: Mar. 18, 2003

(54) INTRAOCULAR ELECTRODE

(75) Inventors: Robert J. Greenberg, Los Angeles, CA (US); Joseph H. Schulman, Santa Clarita, CA (US)

(73) Assignee: Second Sight, LLC, Santa Clarita, CA (US)

( * ) Notice: Subject to any disclaimer, the term of this patent is extended or adjusted under 35 U.S.C. 154(b) by 0 days.

(21) Appl. No.: 09/924,282

(22) Filed: Aug. 8, 2001

(65) Prior Publication Data

US 2002/0002381 A1 Jan. 3, 2002

Related U.S. Application Data

(62) Division of application No. 09/658,160, filed on Sep. 8, 2000, and a division of application No. 09/225,267, filed on Jan. 5, 1999, now Pat. No. 6,165,192.

(51) Int. Cl.$^7$ .............................................. A61B 17/34
(52) U.S. Cl. ...................... 606/185; 606/186; 600/373
(58) Field of Search .................... 600/373, 587, 600/546, 554, 585, 547, 372; 604/361, 362; 606/184, 185, 186

(56) References Cited

U.S. PATENT DOCUMENTS

| | | |
|---|---|---|
| 4,837,049 A | 6/1989 | Byers et al. |
| 4,920,968 A * | 5/1990 | Takase .................. 600/373 |
| 4,969,468 A | 11/1990 | Byers et al. |
| 5,109,844 A | 5/1992 | de Juan, Jr. et al. |
| 5,215,088 A | 6/1993 | Normann et al. |
| 5,361,760 A | 11/1994 | Normann et al. |
| 5,452,716 A * | 9/1995 | Clift .................... 600/373 |
| 5,895,415 A | 4/1999 | Chow et al. |
| 5,935,155 A | 8/1999 | Humayun et al. |

FOREIGN PATENT DOCUMENTS

WO    WO 00/67676    11/2000

* cited by examiner

*Primary Examiner*—Kevin T. Truong
(74) *Attorney, Agent, or Firm*—Scott B. Dunbar

(57) ABSTRACT

This invention is a method and apparatus for implanting retinal tacks and retinal electrode element with spiked electrodes. In one aspect of the invention, a tack suitable for insertion into the retina is driven into the retina by the repeated minute blows from the rapid contractions and expansions of the piezoelectric crystal. In a different aspect of the invention, a retinal electrode element with spiked electrodes suitable for insertion into the retina is driven into the retina by the repeated minute blows from the rapid contractions and expansions of the piezoelectric crystal. In another aspect of the invention, a single, short impulse is used to drive the tack home. In a different aspect of the invention, a single, short impulse is used to drive the retinal electrode element with spiked electrodes home. With this mode of tack and electrode element implanting, a remotely placed driver couples its motion to the tack using a thin, elongated tube filled with a suitable hydraulic fluid.

12 Claims, 4 Drawing Sheets

INTRAOCULAR ELECTRODE

CROSS REFERENCE TO RELATED APPLICATIONS

This application is a division of Ser. No. 09/658,160 filed Sep. 8, 2000 now pending, a division of Ser. No. 09/225,267 filed Jan. 5, 1999, now U.S. Pat. No. 6,165,192.

BACKGROUND OF THE INVENTION

1. Field of the Invention

This invention relates to implanting retinal tacks using a piezoelectric driver. In another embodiment it relates to implanting a retinal implant with spike-like electrodes, using a piezoelectric driver. It also relates to the use of a remote impulse driver, connected to a tack in a tack-holder, by a hydraulic fluid. In another embodiment it relates to the use of a remote impulse driver, connected to a retinal implant with spike-like electrodes in an implant-holder, by a hydraulic fluid.

2. The Prior Art

An example of a preexisting tool for implanting retinal tacks is Sinnett, U.S. Pat. No. 4,784,138; and No. 4,712,550. Actual laboratory experience with the Sinnett tool found that an apparatus like Sinnett's applied too much force to the retina. Consequently, this tool has a restricted functional ability to tack devices to the back of the eye.

SUMMARY OF THE INVENTION

This invention is a method and apparatus for implanting retinal tacks. In one aspect of the invention, a tack suitable for insertion into the retina is driven into the retina by the repeated minute blows from the rapid contractions and expansions of the piezoelectric crystal.

In another aspect of the invention, a single, short impulse is used to drive the tack home. With this mode of tack driving, a remotely placed driver couples its motion to the tack using an elongated tube filled with a suitable hydraulic fluid.

Similar method and apparatus is used for implanting a retinal implant having spike-like electrodes. In another aspect of the invention, a retinal implant with spike-like electrodes is driven into the retina (or other suitable tissue which can hold the implant) by the repeated minute blows from the rapid contractions and expansions of the piezoelectric crystal. The spiked electrodes may have a barbed point so as to facilitate their remaining imbedded in the interior wall of the back of the eye.

In a different aspect of the invention, a single, short impulse is used to drive the retinal implant with spiked-electrodes home. With this mode of driving the spiked-electrode retinal implant, a remotely placed driver couples its motion to the implant using an elongated tube filled with a suitable hydraulic fluid. The spiked electrodes are driven into tissue suitable to hold it in place. The spike electrodes may have a type of barb point on them so as to facilitate their remaining imbedded in the interior wall of the back of the eye. A plurality of spike electrodes may be dummy electrodes in that they function only as mechanical anchors, and do not function as electrodes. Thus, four corner dummy electrodes may anchor the retinal electrode element, which may even have the rest of its electrodes shorter than the dummy electrodes or have the rest of the electrodes as flat electrodes.

BRIEF DESCRIPTION OF THE DRAWINGS

The above and other features and advantages of the invention will be more apparent from the following detailed description wherein.

DESCRIPTION OF THE PREFERRED EMBODIMENTS

The following description is of the best mode presently contemplated for carrying out the invention. This description is not to be taken in a limiting sense, but is merely made for the purpose of describing the general principles of the invention. The scope of the invention should be determined with reference to the claims.

Figure 1:
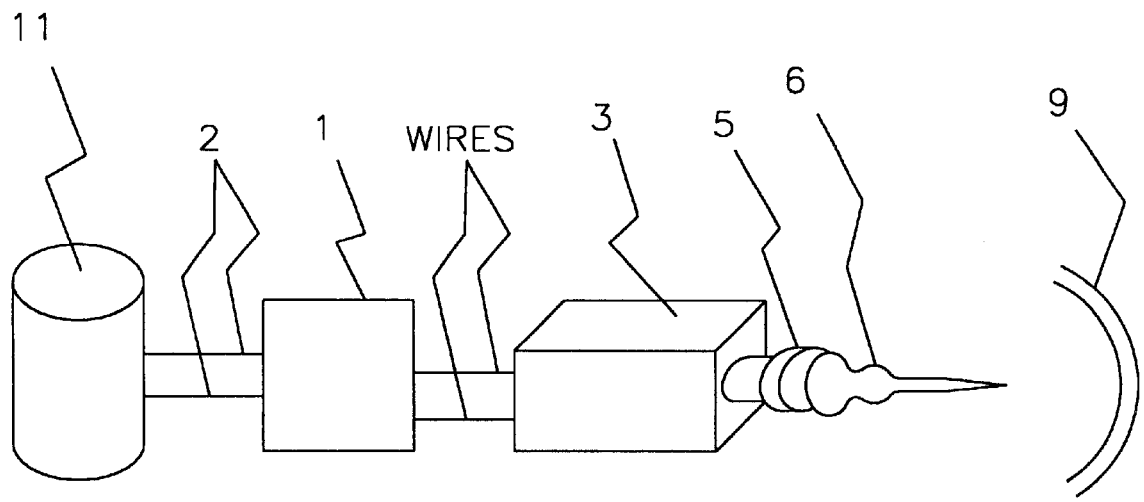
FIG. 1 shows a retinal tacker that uses an electronically driven piezoelectric crystal.

This invention is a method and apparatus for implanting retinal tacks and into the retina, as well as for doing the same for retinal implants with spike electrodes. FIG. 1 shows a retinal tacker that uses a piezoelectric crystal (3) electrically driven by electrical source (11), which may be a battery. The electrical or electronics unit (1) also contains required resonant elements. The piezoelectric crystal undergoes a constriction-relaxation cycle under the application of an alternating current via wires (2). Thus, the piezoelectric crystal (3) is set into a vibrating motion that is mechanically coupled, by the tack holder (5) to the retinal tack (6).

Figure 2:
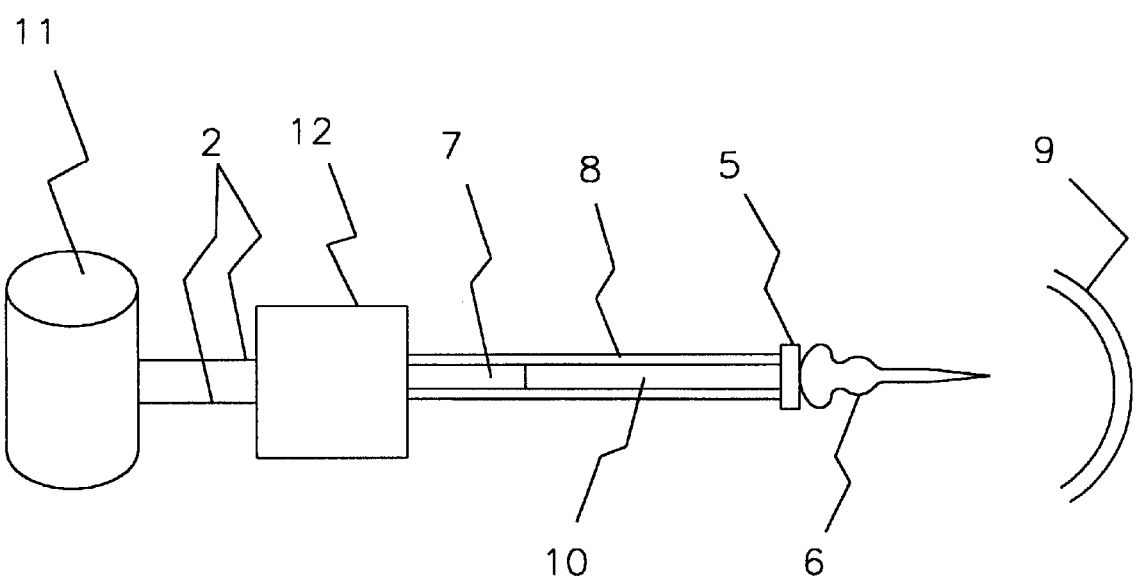
FIG. 2 shows a retinal tacker that uses a remote impulse driver connected by a tube filled with hydraulic fluid.

A mechanical system, (5) in FIG. 1 or FIG. 2, holds a retinal tack (6). The tack is made from titanium or from a similarly sufficiently biologically non-reactive material. The material used must be sufficiently non-reactive with the back of the eyeball (sclera) where the tack is implanted, as well as the retina itself, and the vitreous humor fluid of the eye.

The tack is inserted into the eye with the holder and placed against the retinal surface. As shown, in FIG. 1, when the tack (6) is touching the retinal surface (9), the electronic drive circuitry (1) is turned on which causes the piezoelectric crystal (3) to vibrate. The vibrating crystal is mechanically coupled to the tack (6) and allows the surgeon to insert the tack (6) into the retina (9) with less force. The vibrations allow the hard tack to enter the soft tissue of the retina instead of pushing it out of the way.

Advantageously, the vibrations make it easier to insert the tack into the sclera, since the relaxation time of the organic tissues is shorter for breaking and longer for bending. Each vibration imparts a quick cutting effect to the leading point of the tack. Although each vibration is a short movement, the high rate of vibration results in effectively a longer, but individually for each vibration, a quick cutting action. The longer time comprises the sum of the individual forward vibration times and the non-forward part of the vibration stroke.

Figure 3:
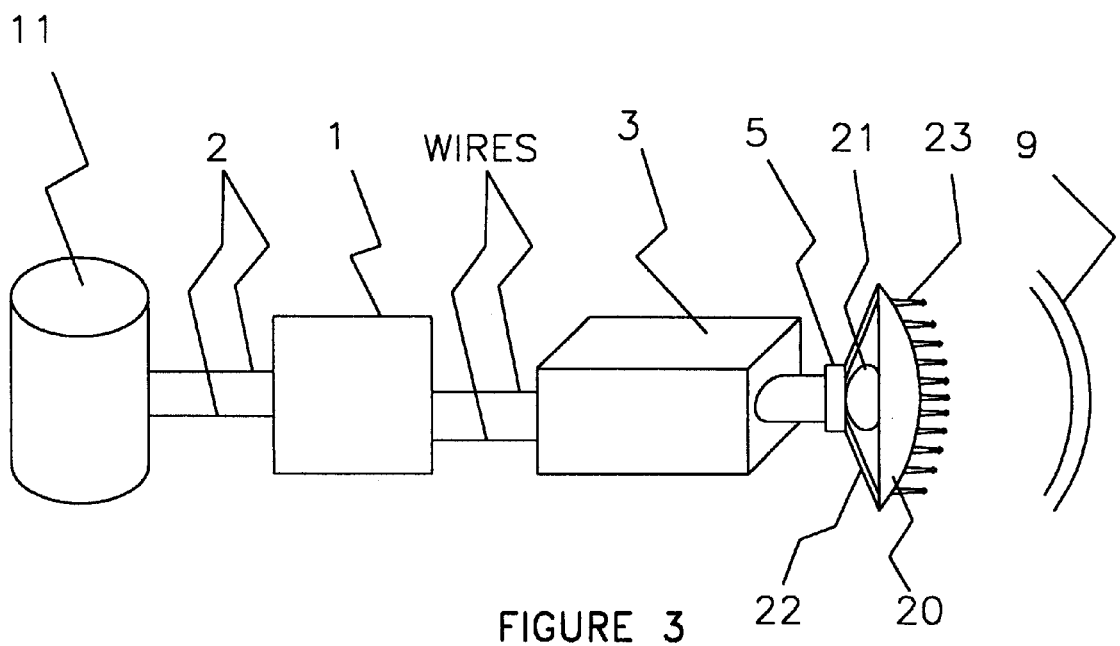
FIG. 3 shows a retinal implant tacker, for an implant with spiked electrodes, that uses an electronically driven piezoelectric crystal.

FIG. 3 illustrates the piezo-electric driver (FIG. 1) for a retinal tack (FIG. 1, (6)) applied to the retinal implant (20) with spike electrodes (23). In this embodiment the head (21) of a retinal tack (5) is mounted on or near the center of the retinal implant (20). The holder (5) fits the head-of-tack fitting (21) and the operation is similar to driving a single tack. A plurality of arms (22) emanating and anchored to the holder (5) act to steady the implantable electrode element (20). One embodiment of this invention uses four arms (22) to steady the four corners of a rectangular shaped back surface of the electrode element (20). In FIGS. 1,2,3 and 4, the electrode element (20) is shown with a curvature so as to conform to the curvature of the retina (9). However, the large number of spike electrodes (23) can require a larger voltage input into the piezo-electric crystal so as to produce a proportionally larger force (approximately). In another aspect of the invention, a plurality of spike electrodes may be dummy electrodes in that they function only as mechanical anchors, and do not function as electrodes. Thus, four corner dummy electrodes may anchor the retinal electrode element, which may even have the rest of its electrodes shorter than the dummy electrodes or have the rest of the electrodes as flat electrodes.

FIG. 2 shows a retinal tacker that uses a piston (7) electrically driven by electrical source (11), which may be a battery. In this alternative embodiment, the electronic circuitry (12) is turned on causing a piston (7) to impact hydraulic fluid (10) in a thin tube (8). The sudden impulse of the piston (7) is transmitted to the tack (6) being held in its tack holder (5). This sudden impulse drives the tack (6) into the retinal wall (9). Advantageously, the sudden impulse is such that a large amount of force is transmitted in a very short time. Consequently the tack is forced into the desired organic tissue and does not just push it back or bend it.

Figure 4:
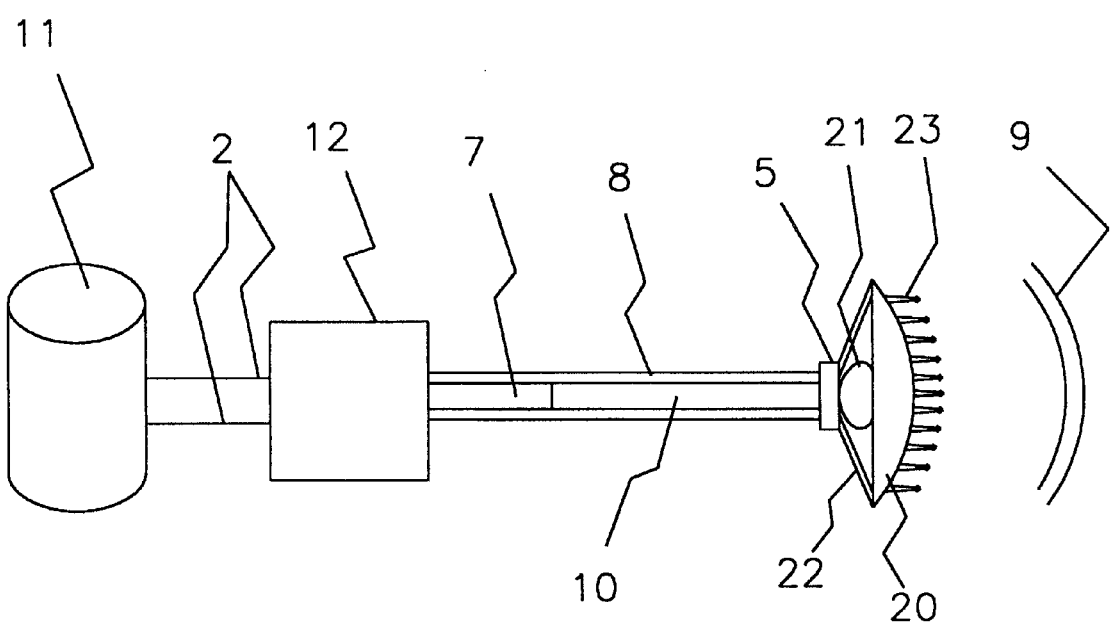
FIG. 4 shows a retinal implant tacker, for an implant with spiked electrodes, which uses a remote impulse driver connected by a tube filled with hydraulic fluid.

FIG. 4 illustrates the hydraulic driver (FIG. 2) for a retinal tack (FIG. 2, (6)) applied to the retinal implant (20) with spike electrodes (23). In this embodiment the head (21) of a retinal tack (FIG. 2, (6)) is mounted on or near the center of the retinal implant (20). The holder (5) fits the head-of-tack fitting (21) and the operation is similar to driving a single tack (FIG. 2, (6)). However, the large number of spike electrodes (23) can require either a larger voltage input into the piston driving circuitry or a larger fluid driving piston so as to produce an approximate proportionally larger force. A plurality of arms (22) emanating and anchored to the holder (5) act to steady the implantable electrode element (20). One embodiment of this invention uses four arms (22) to steady the four corners of a rectangular shaped back surface of the electrode element (20). In FIGS. 1,2,3 and 4, the electrode element (20) is shown with a curvature so as to conform to the curvature of the retina (9).

Figure 5A:
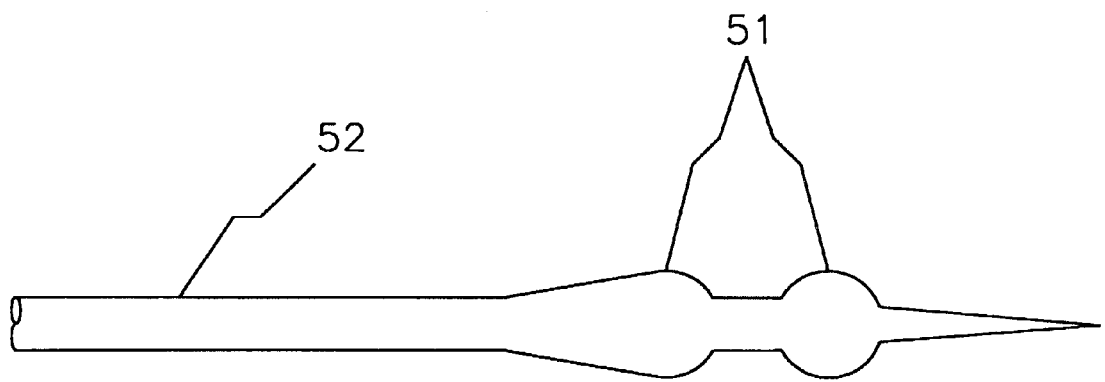
FIG. 5a shows a barb similar to a retinal tack for use with the spiked electrodes.
Figure 5B:
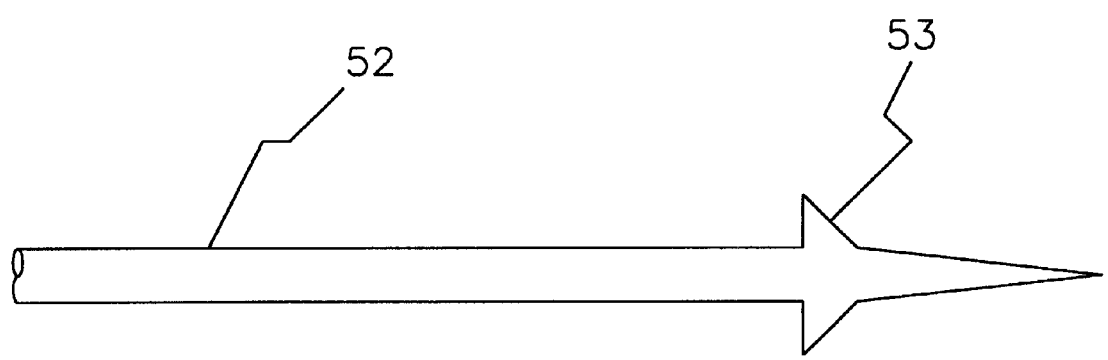
FIG. 5b shows a barb similar to a fishhook for use with the spiked electrodes.
Figure 6A:
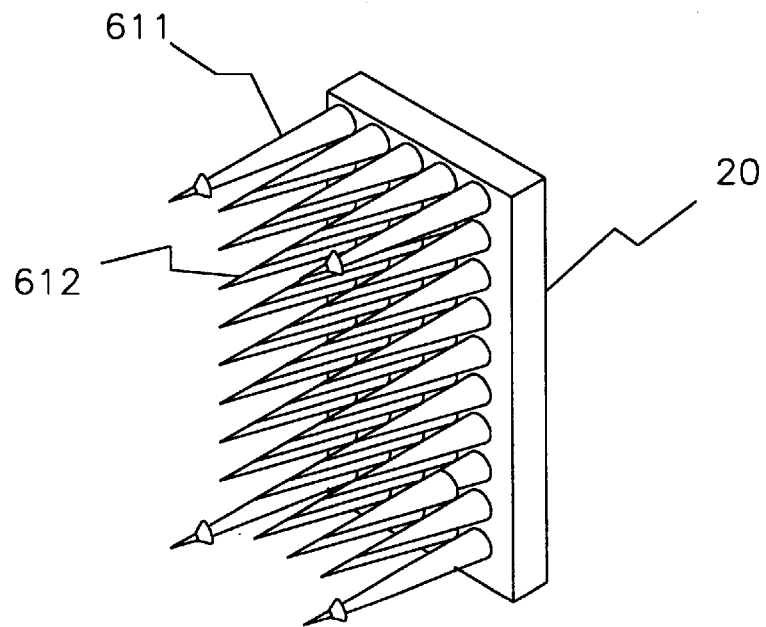
FIG. 6a shows a plurality of dummy non-working electrodes that extend beyond the lengths of the electrodes and anchor the retinal electrode element to the back of the eyeball.
Figure 6B:
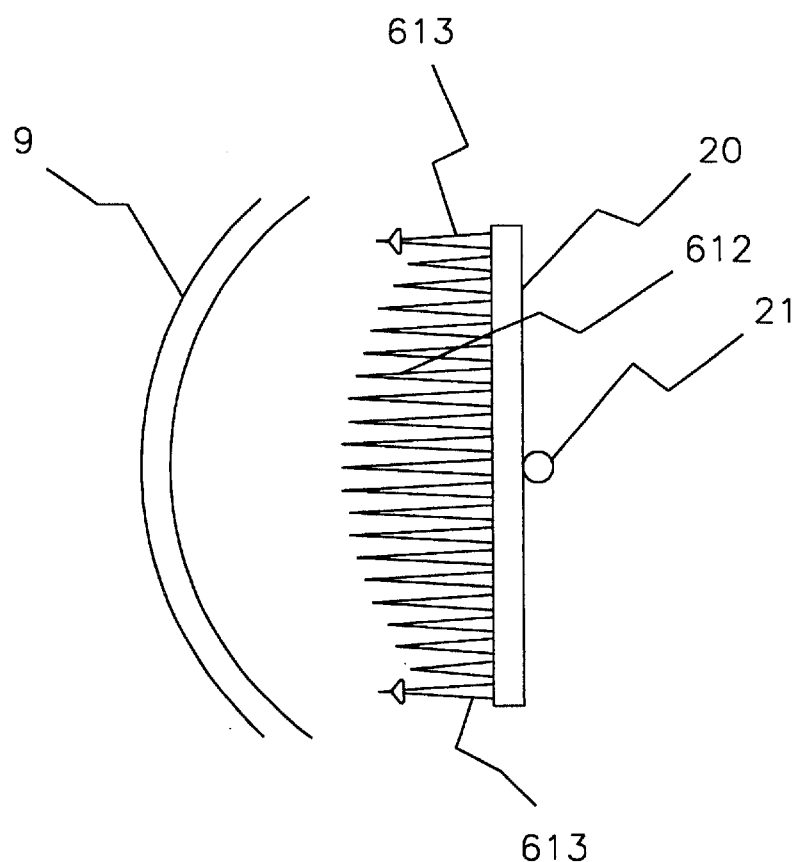
FIG. 6b shows a plurality of dummy non-working electrodes that extend sufficiently beyond the relevant lengths of the electrodes which are proportioned to the curvature of the retinal and anchor the retinal electrode element to the back of the eyeball.

Two types of barbs for the retinal element's spike electrodes are shown in FIG. 5. FIG. 5a shows a barb (51) similar to a retinal tack. The tack-type barb (51) is formed as part of the spike electrode (52). FIG. 5b shows a barb (53) similar to a fishhook barb. The fishhook-type barb (53) is formed as part of the retinal element's spike electrodes (52). The barb help the electrode stay anchored in the tissue in which it has been driven by one of the embodiments of this retinal tacker invention. A plurality of spike electrodes may be dummy electrodes in that they function only as mechanical anchors (FIGS. 6a and b), and do not function as electrodes. Thus (FIG. 6a), four corner dummy electrodes (611) may anchor the retinal electrode element (20), which may even have the rest of its electrodes (612) shorter than the dummy electrodes (611) or have the rest of the electrodes (FIG. 6b) as retina matching curved envelope electrodes (613). The head-of-tack fitting (21) is also shown with the retina (9).

The retinal tack or the spike electrode with its barb may attach a retinal electrode element in an epiretinal or subretinal position. It may attach other items and the retina as well as a retinal electrode element or other eye implantable element to the back of the interior of the eyeball, in any order, impaled on the tack or the barbed spike electrode, dummy or real. The practical limitation is placed by the length of the tack or barbed spike electrode, real or dummy and by the holding power of the imbedded tack or barbed spike electrode, real or dummy.

While the invention herein disclosed has been described by means of specific embodiments and applications thereof, numerous modifications and variations could be made thereto by those skilled in the art without departing from the scope of the invention set forth in the claims.

What is claimed is:

1. An electrode element comprising:
    a base;
    a plurality of electrodes on said base; and
    a barbed, elongated spike electrode on said base so as to keep said electrode element from pulling out of living tissue in which it is implanted.

2. The electrode element of claim 1 wherein said barbed, elongated spike electrode is a non-working electrode.

3. The electrode element of claim 1 further comprising a plurality of barbed, elongated spike electrodes, on said base, that extend beyond the lengths of said plurality of electrodes.

4. The electrode element of claim 3 wherein said plurality of barbed elongated spike electrodes are disposed around the periphery of said electrode element.

5. The electrode element of claim 1 wherein said plurality of electrodes form a curved contact area.

6. The electrode element of claim 1 adapted for implantation in an eye.

7. A retinal electrode element for implantation in an eyeball comprising:
    a base;
    a plurality of electrodes on said base; and
    a plurality of barbed elongated spike electrodes, on said base, so as to keep said retinal electrode element from pulling out the eyeball in which it is implanted.

8. The retinal electrode element of claim 7 wherein said plurality of barbed, elongated spike electrodes are non-working electrodes.

9. The retinal electrode element of claim 7 wherein said plurality of barbed, elongated spike electrodes extend beyond the lengths of said plurality of electrodes.

10. The retinal electrode element of claim 7 wherein said plurality of barbed elongated spike electrodes are disposed around the periphery of said electrode element.

11. The retinal electrode element of claim 7 wherein said plurality of electrodes form a curved contact area.

12. The retinal electrode element of claim 7 wherein said plurality of electrodes are spike electrodes.

* * * * *